United States Patent [19]
Hunter et al.

[11] 3,955,994
[45] May 11, 1976

[54] CEMENTITIOUS STRUCTURES OF IMPROVED DURABILITY

[75] Inventors: Byron A. Hunter, Woodbridge; John W. Zukel, New Haven, both of Conn.

[73] Assignee: Uniroyal Inc., New York, N.Y.

[22] Filed: Dec. 16, 1974

[21] Appl. No.: 533,394

Related U.S. Application Data

[62] Division of Ser. No. 236,763, March 21, 1972, abandoned.

[52] U.S. Cl................................. 106/90; 106/97
[51] Int. Cl.².......................................... C04B 7/02
[58] Field of Search ................. 106/12, 90, 97, 3.4, 106/3.5

[56] References Cited
UNITED STATES PATENTS 3,817,767  6/1974  Bozer et al............................ 106/90

*Primary Examiner*—J. Poer
*Attorney, Agent, or Firm*—Willard R. Sprowls

[57] ABSTRACT

Cementitious structures characterized by improved durability and weather resistance are obtained by: Incorporating alkyl and alkenyl succinic acids, their anhydrides, acid esters, acid amides, halogenated compounds and salts, into cementitious mixtures prior to setting; applying said succinic compounds onto concrete subsequent to setting; or by a combination of the forgoing steps; said alkyl and alkenyl substituents containing from 8 to 40 carbon atoms.

4 Claims, No Drawings

CEMENTITIOUS STRUCTURES OF IMPROVED DURABILITY

This is a division, of application Ser. No. 236,763, filed Mar. 21, 1972, now abandoned.

BACKGROUND OF THE INVENTION

The invention is concerned with a practical method for preventing the deterioration of concrete. It is especially directed toward the deterioration of concrete which results from the influence of weather and temperature fluctuations. The invention is also aimed at preventing the deterioration of concrete attributed to the harmful action of deicing agents such as sodium chloride or calcium chloride. Such deicing agents are widely employed on highways, bridge decks, sidewalks, etc. in spite of the clearly demonstrated fact that these materials are deleterious and accelerate spalling and breaking up of concrete.

Numerous materials have been used or suggested as surface treatments to improve the weatherability of concrete. These include fats, fatty acids, fatty acid salts, paraffins, waxes, greases, rosin, mineral and vegetable oils, silicones, bituminous materials, coal tar pitch, plastic coatings, polymers, etc., however, most of these have limited effectiveness. For instance, linseed oil-kerosene mixtures have been favored as a surface treatment to retard freeze-thaw deterioration. However, comparatively large amounts of oil are required and more effective and economical measures are desireable.

PRIOR ART

A recent patent (U.S. Pat. No. 3,438,804) describes the use of polyisobutenyl succinic anhydride as a useful material for providing water repellency to masonry materials. This polymeric material is described as the reaction product of maleic anhydride with a polyisobutylene of molecular weights between 800 and 1200. The molecular weight of the product (which includes that of maleic anhydride) lies between 900 and 1300. When coated on concrete, this polyisobutenyl succinic anhydride is only moderately effective insofar as preserving the durability and weathering resistance of concrete.

Thus the principal challenge in the art is to provide methods for treating cementitious materials in order to more effectively prevent weathering and deterioration. Complicating or compounding this challenge is the existing problem of resolving rapid deterioration of concrete under varying weather conditions such as alternate freezing and thawing; and the troubling problem of contending with the deleterious action of deicing agents such as sodium chloride and calcium chloride upon concrete, during such freezing and thawing cycles.

SUMMARY OF THE INVENTION

It has been found that concrete may be improved to better resist weathering by treating concrete with compounds of alkyl and alkenyl succinic acids, their anhydrides, acid esters, acid amides, halogenated compounds and salts, when the alkyl and alkenyl substituents contain from 8 to 40 carbon atoms. The method of treatment entails: incorporating the compounds into the cementitious mix; coating the compounds on a concrete surface, or a combination of the preceding steps.

The principal object of the invention is to provide treatments for rendering concrete and masonry more resistant to weathering.

Other objects and advantages of the invention will become apparent in the descriptions and examples hereinafter appearing.

DETAILED DESCRIPTION OF THE INVENTION

The invention appreciates that certain succinic acid derivatives are highly effective in preventing deterioration of concrete under varying weather conditions. More precisely, it has been found that long chain aliphatic succinic acid compounds and their derivatives are effective against such deterioration. The particular groups are the primary, secondary and tertiary alkyl or alkenyl hydrocarbon radicals. Thus, it has been found that alkenyl succinic anhydride compounds prepared by reacting maleic anhydride and olefins containing at least 8 carbon atoms can be effectively used to preserve concrete. The carbon chain in the olefin can be straight or normal, or the chain may be branched. The olefinic linkages may be terminal and/or internal. However, any olefin that contains at least 8 carbon atoms and is reactive towards maleic anhydride can be used. Examplary of olefins which may be employed are: diisobutylene, tripropylene, tetrapropylene, triisobutylene, octene-1, nonene-1, decene-1, undecene-1, dodecene-1, tridecene-1, tetradecene-1, pentadecene-1, hexadecene-1, heptadecene-1, octadecene-1 and eicosene-1. Mixtures of olefins may also be used. In the context of the invention, the range of carbon lengths in the alkyl and alkenyl substituents of the succinic compounds is from 8 to 40 carbon atoms.

The chemical compounds which are useful for the purpose of the invention are represented by the following general structure:

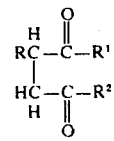

Where R may be an alkyl, haloalkyl or an alkenyl group having from 8 to 40 carbon atoms, $R^1$ and $R^2$ may be the same or different, and may be $-NR^3R^4$ or $-OR^5$, wherein $R^3$, $R^4$ and $R^5$ may be the same or different, and may be hydrogen or an alkyl group having from 1 to 3 carbon atoms - provided that at least one of the $R^1$ and $R^2$ groups is a hydroxy moiety; and their ammonia, amine or metal salts, or $R^1$ and $R^2$ combined represent a single divalent oxygen atom.

While the broad range of operable succinic compounds in the broad inventive context may contain from eight to forty carbon atoms in the alkyl and alkenyl substituents, eight to twenty eight carbon atoms are preferred, and eleven to twenty carbon atoms are most preferred. In a particular form of application, however, the preferred length of the hydrocarbon chain will vary with the mode of use.

For example, incorporation of the protective succinic acid derivatives in the concrete mixer is conveniently accomplished by measuring out the desired amount, as a concentrated aqueous solution, and combining it with the water to be added to the mix. For this mode of use, the water soluble salt forms of the succinic acid compounds are preferred. Succinic acid derivatives having less than twenty carbon atoms in the alkyl or alkenyl groups exhibit better water solubility than those of higher molecular weight. Thus, compounds with alkyl or alkenyl substituents in the eight to fourteen carbon atom range are generally preferred.

Similarly, when the derivatives are to be used in aqueous solution as a surface treatment for cured concrete, salts of compounds with alkyl or alkenyl substituents in the 8 to 14 carbon atom range are preferred.

When the succinic acid derivatives are applied from organic solvent solutions (i.e. xylene, kerosene, turpentine, mineral spirits, and alcohols) to the surface of cured concrete, the best results are accomplished when using an organic solvent soluble form. In this form, the chain length of the hydrocarbon group is less restricting. Thus, derivatives containing as few as eight carbon atoms in the substituent or as high as forty carbon atoms may be used, as long as they are soluble in the particular organic solvent. In general, in the organic solvent form of usage, best results are obtained if the substituent groups are not higher than twenty eight carbon atoms.

On a percent by weight basis based upon the ingredients in the cement mix, the amount of succinic compound which may be utilized when added directly in the cement mix may range from about 0.005 to 10%; preferably from 0.01 to 3%; and most preferably from 0.05 to 1%.

The succinic compounds can be incorporated into the cementitious mix in the dry form or as a water solution, prior to setting. In other instances the compounds are first incorporated into the cementitious mix prior to setting and also coated on the concrete substrate subsequent to setting, from an aqueous or organic solution or from an emulsion. In still another instance, the compounds are merely coated onto the concrete substrate, using aqueous or organic solutions or an emulsion.

When applying the succinic compounds as an aqueous solution to the surface of the cement or cured cementitious structure, the best results are obtained when R represents 8 to 20 carbon atoms.

However, when applying the succinic compounds onto a cement surface from an organic solvent solution, the best results are obtained when R represents 11 to 28 carbon atoms.

As set forth above, the succinic compounds may be added in the non-salt or salt form. When added in the salt form, exemplary metals which may be employed are: sodium, potassium, lithium, magnesium, calcium, barium, aluminum, iron, copper, zinc, etc. The alkali metal salts of the succinic compounds are particularly useful in this context as they exhibit good water solubility and may be added in aqueous solution to a concrete mix and also coated onto the set or finished concrete structure. Ammonium and amine salts may also be used.

Typical but non-limiting examples of succinic compounds which may be employed to preserve concrete are: n-octenylsuccinic anhydride, n-dodecenylsuccinic anhydride, n-octadecenylsuccinic anhydride, n-eicosenyl succinic anhydride, t-octenylsuccinic anhydride, t-nonenylsuccinic anhydride, t-tetrapropenylsuccinic anhydride, n-octylsuccinic anhydride, n-dodecylsuccinic anhydride, n-octadecylsuccinic anhydride, n-eicosyl succinic anhydride; n-octenylsuccinic acid, t-octenylsuccinic acid, t-nonenylsuccinic acid, t-tetrapropenylsuccinic acid, n-octylsuccinic acid, n-dodecylsuccinic acid, n-tetradecylsuccinic acid, n-hexadecylsuccinic acid, and n-octadecylsuccinic acid; dibromododecylsuccinic anhydride, dichlorododecylsuccinic anhydride, dichlorooctadecylsuccinic anhydride, dichloro-t-octylsuccinic anhydride, dichlorododecyl succinic acid and dichlorooctadecylsuccinic acid; disodium dodecenylsuccinate, disodium tetradecenylsuccinate, disodium hexadecenylsuccinate, disodium dichlorooctadecylsuccinate, diammonium dodecyl-succinate, diammonium dodecenylsuccinate, diammonium hexadecenylsuccinate, diammonium octadecylsuccinate, diammonium dichlorotetradecylsuccinate, ammonium dodecylsuccinamate, ammonium dodecenylsuccinamate, ammonium tetradecenylsuccinamate, ammonium hexadecenylsuccinamate, ammonium octadecenylsuccinamate, ammonium tetrapropenyl succinamate and methyl ammonium-N-methyldodecenylsuccinamate.

The benefits obtained by treating cementitious materials with the succinic acid derivatives hereinabove set forth are illustrated in the following examples, which are descriptive of, but not limiting upon the invention.

EXAMPLE I

A freeze thaw test was conducted upon concrete blocks in the presence of a 3% solution of sodium chloride, in order to demonstrate the preserving effects of incorporated succinic compounds. A typical dry mix was prepared by blending 600 grams of gravel, 400 grams of sand, 200 grams of Portland cement.

The dry mix was combined with 136 grams of water and thoroughly mixed to give a typical workable concrete mix. The entire mass was evenly distributed in a plastic tray compartmentalized into 16 cubical units. The tray was then placed in a shallow pan of water (the water level well below the top of the tray) and allowed to cure for two days. The cubes were removed from the tray and allowed to stand for a week in a covered beaker containing water vapor. The cubes were then allowed to stand in air for at least thirty days.

Similar concrete cubes were prepared with the exception that the water was replaced by 136 cubic centimeters of a 1% water solution of the chemicals listed in Table I. The concrete cubes were cured in the manner described above.

One cube was taken from each batch of concrete described (including that prepared from straight water and those prepared with the 1% solution of chemicals of Table I). The cubes were placed individually in small wide mouthed screw top jars (4 oz.) and covered with a 3% sodium chloride solution. The top of each jar was secured. The jars were placed in a freezer overnight at −10 to −15°C. The next day the frozen samples were removed and allowed to thaw at room temperature. The samples were alternately frozen and thawed for numerous cycles and the appearance of the cubes were observed after each cycle. The observations obtained are shown in Table I.

EXAMPLE II

Same as Example I with the exception that prior to treatment with the sodium chloride deicing solution, the cured or set concrete is surface treated with a 3% toluene solution of the alkenyl succinic anhydrides of Table II until the surface is completely wet. The cubes were allowed to stand overnight to allow the solvent to evaporate. The preservation characteristics were similar to those shown in Table I.

EXAMPLE III

A concrete mix was prepared by blending 600 grams of gravel, 400 grams of sand, 200 grams of Portland cement and 136 grams of water. After thorough mixing, the mixture was poured into a 16 compartment plastic tray and cured as described in Example I.

After 30 days of drying in air, the cubes were individually placed into beakers and covered with 3% solutions of various succinic anhydride compounds in xylene. After one-half hour the cubes were removed from the solution and xylene was allowed to evaporate overnight. The cubes were individually placed into 4 oz. jars and covered with a 3% sodium chloride solution. The covers were secured and the jars and contents were subjected to repeated-freeze-thaw cycles as described in Example I. The effects of these compounds in protecting the concrete from freeze-thaw degradation in the presence of sodium chloride are shown in Table III.

EXAMPLE IV

Same as Example II, except that surface treatment was conducted with 3% aqueous solutions of the succinic compounds of Table IV. The results were comparable to those in Example II.

EXAMPLE V

Concrete cubes prepared as described in Example III were surface treated with isopropanol solutions of the succinic acid compounds of Table V, and subjected to freeze-thaw tests in 3% sodium chloride solutions. The surface treatment, drying and testing of the cubes were conducted as described in Example III. The effects of the various treatments are shown in Table V.

EXAMPLE VI

The polyisobutenyl succinic anhydride polymers set forth in U.S. Pat. No. 3,438,804 were compared to the succinic compounds of the instant invention for an assessment of the relative effectiveness in preventing deterioration of concrete under freeze-thaw weathering conditions. Concrete blocks were prepared by mixing 600 grams of gravel, 400 grams of washed sand, 200 grams of Portland cement and 136 grams of water and puring the well mixed composition into a polyethylene tray compartmentalized into 16 units. After curing for two days in a moist atmosphere the cubes were separated from the polyethylene tray and allowed to cure for 28 days more in a moist atmosphere. Subsequently, they were dried at room temperature in the laboratory for 30 days more. Individual blocks were placed in beakers of 1% hexane (or isopropanol) solutions for a period of three hours and were then removed and allowed to dry overnight. At this point each of the treated cement blocks were placed in individual 4 oz. wide mouth jars; covered with 3% sodium chloride solutions; and then covered to prevent evaporation. The marked jars were then placed in a freezer and brines surrounding the blocks were allowed to freeze solid. The jars were then removed from the freezer and allowed to thaw and warm up to room temperature. The blocks were examined for evidence of cracking or deterioration. The blocks were then subjected to alternate freezing and thawing and examined after each freeze-thaw cycle. The results of the treatments are summarized in Table VI.

On weight basis, the surface coating may be performed with solutions ranging from about 0.1% to 5% of the succinic compound; preferably from about 0.5% to 4%; and most preferably from about 1% to 3%. The thickness of the coating does not seem to be critical, and does not constitute a part of the invention.

Table I

Freeze-Thaw Tests in 3% Sodium Chloride Solution
(Freezing at −10 to −15°C.)

| Chemical (1% in water) | Results | | | | |
|---|---|---|---|---|---|
| None | 2nd cycle - bad cracks; 3rd cycle - badly disintegrated | | | | |
| Disodium dodecenylsuccinate | No deterioration through | 12 | cycles; | slight spalling at | 14 cycles |
| Disodium tetradecenylsuccinate | " | 11 | " ; | " | 17 " |
| Disodium hexadecenylsuccinate | " | 16 | " ; | " | 17 " |
| Disodium dichlorooctadecylsuccinate | " | 20 | " ; | | |
| Diammonium dodecylsuccinate | " | 7 | " ; | " | 18 " |
| Diammonium dodecenylsuccinate | " | 9 | " ; | " | 12 " |
| Diammonium hexadecenylsuccinate | " | 9 | " ; | " | 20 " |
| Diammonium octadecylsuccinate | " | 7 | " ; | " | 8 " |
| Diammonium dichlorotetradecylsuccinate | " | 13 | " ; | | |
| Diammonium dichlorohexadecylsuccinate | " | 10 | " ; | " | 11 " |
| Ammonium dodecylsuccinamate | " | 18 | " ; | | |
| Ammonium dodecenylsuccinamate | " | 10 | " ; | " | 12 " |
| Ammonium tetrapropenylsuccinamate | " | 9 | " ; | " | 18 " |
| Ammonium hexadecenylsuccinamate | " | 7 | " ; | " | 8 " |
| Methyl ammonium-N-methyldodecenyl-succinamate | " | 6 | " ; | " | 8 " |

Table II

Alkenyl Succinic Anhydrides (dissolved in toluene)

| Chemical |
|---|
| n-Octenyl succinic anhydride |
| n-Dodecenyl succinic anhydride |
| n-Octadecenyl succinic anhydride |
| n-Eicosenyl succinic anhydride |
| tert. Octenyl succinic anhydride |
| tert. Nonenyl succinic anhydride |
| tert. Tetrapropenyl succinic anhydride |
| n-Octyl succinic anhydride |
| n-Dodecyl succinic anhydride |
| n-Octadecyl succinic anhydride |
| n-Eicosyl succinic anhydride |

Table III

Freeze-Thaw Tests in 3% Sodium Chloride Solution

| Chemical (3% in Xylene) (applied to surface) | | Results | | |
|---|---|---|---|---|
| None | | Cracks (2 cycles); disintegrated (4 cycles) | | |
| N-Butyl | succinic anhydride | Intact thru | 7 cycles; | " (9 " ) |
| n-Butenyl | " | " | 7 " ; | " (10 " ) |
| n-Hexenyl | " | " | 8 " ; | " (13 " ) |
| n-Octenyl | " | " | 9 " ; | slight surface spall at 15 cycles |
| n-Decenyl | " | " | 12 " ; | cracks at 14 cycles |
| Tetrapropenyl | " | " | 20 " ; | surface spall at 21 cycles |
| $C_{11}$–$C_{14}$ mixed alkenyl | " | " | 17 " ; | cracks at 19 cycles |
| Eicosenyl | " | " | 11 " ; | slight surface spall at 20 cycles |
| $C_{22}$–$C_{28}$ mixed alkenyl | " | " | 16 " ; | surface spall at 16 cycles |
| $C_{30}$ + mixed alkenyl | " | " | 14 " ; | cracks at 16 cycles |
| Dichlorotetradecyl | " | " | 14 " ; | surface spall at 16 cycles |
| Dibromo octadecyl | " | " | 17 " ; | " 19 " |

Table IV

Sodium Salts of Alkenyl Succinic Acids

CUZ,5/10 Chemical
Disodium salt of n-octenyl succinic acid
Disodium salt of n-dodecenyl succinic acid
Disodium salt of n-octadecenyl succinic acid
Disodium salt of t-nonenyl succinic acid
Disodium salt of n-octyl succinic acid
Disodium salt of n-dodecyl succinic acid
Disodium salt of n-tetradecyl succinic acid
Disodium salt of n-hexadecyl succinic acid
Disodium salt of n-octadecyl succinic acid

Table V

Freeze-Thaw Tests in 3% Sodium Chloride Solution

| Chemical (3% in Isopropanol) | Results |
|---|---|
| None | Cracks 2 cycles; disintegrated 4 cycles |
| Succinic acid | Bad spall 3 cycles; disintegrated 7 cycles |
| Dibromo tetradecyl succinic acid | Intact 11 cycles; cracks 14 cycles |
| Tetradecyl succinic anhydride (probably the isopropyl acid ester) | Intact 14 cycles; spall 16 cycles |
| $C_{11}$–$C_{14}$ mixed Alkenyl succinic acid | Slight spall 8 cycles; spall 15 cycles |

Table VI

| Sample No. | Chemical | Solvent | Results |
|---|---|---|---|
| 1 | Dodecenylsuccinic anhydride | Hexane | No deterioration 9 cycles. |
| 2 | Tetrapropenylsuccinic anhydride | Hexane | No deterioration 9 cycles. |
| 3 | Dodecylsuccinic acid | Hexane | No deterioration 9 cycles. |
| 4 | Dodecylsuccinic acid | Isopropanol | No deterioration 9 cycles. |
| 5 | No treatment | | {Slight cracks 3 cycles. Breaking up at 5 cycles.} |
| 6 | Polyisobutenylsuccinic anhydride (mol. wt. 518) | Hexane | {Slight cracks 4 cycles. Breaking up at 5 cycles.} |
| 7 | Polyisobutenylsuccinic anhydride (mol. wt. 538) | Hexane | {Slight cracks 3 cycles. Breaking up at 5 cycles.} |
| 8 | Polyisobutenylsuccinic anhydride (mol. wt. 1048) (material described in U.S. Pat. No. 3,438,804) | Hexane | {Slight cracks 3 cycles. Breaking up at 5 cycles.} |

It is to be appreciated that the methods outlined above for utilizing the succinic compounds to preserve cement is applicable to all hydraulic cements, including the mixtures of lime, silica, and alumina, or of lime and magnesium, silica and alumina and iron oxide, and various other commonly known hydraulic cements. Consequently the examples above are descriptive of rather than limited to the ambit of the inventive concept.

What is claimed is:

1. A method of improving the durability and freeze-thaw stability of cementitious structures, comprising applying an effective amount of a chemical compound of the general formula:

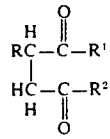

Where R may be an alkyl, haloalkyl or alkenyl group having from 8 to 40 carbon atoms, $R^1$ and $R^2$ may be the same or different, and may be $NR^3R^4$ or -$OR^5$, wherein $R^3$, $R^4$ and $R^5$ may be the same or different, and may be hydrogen or an alkyl group having from 1 to 3 carbon atoms — provided that at least one of the $R^1$ and $R^2$ groups is a hydroxy moiety;
and their ammonia, amine or metal salts, or $R^1$ and $R^2$ combined represent a single divalent oxygen atom; onto the cementitious structure.

2. The method of claim 1, wherein the chemical compound contains from 8 to 30 carbon atoms in the alkyl or alkenyl substituent.

3. A cementitious structure of improved durability and freeze-thaw stability, and having applied upon its surface, an effective amount of a chemical compound of the general formula:

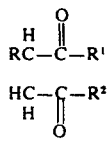

Where R may be an alkyl, haloalkyl or alkenyl group having from 8 to 40 carbon atoms, $R^1$ and $R^2$ may be the same or different, and may be $-NR^3R^4$ or $-OR^5$, wherein $R^3$, $R^4$ and $R^5$ may be the same or different, and may be hydrogen or an alkyl group having from 1 to 3 carbon atoms - provided that at least one of the $R^1$ and $R^2$ groups is a hydroxy moiety; and their ammonia, amine or metal salts, or $R^1$ and $R^2$ combined represent a single divalent oxygen atom.

4. A cementitious structure as in claim 3, wherein the chemical compound contains from 8 to 30 carbon atoms in the alkyl or alkenyl substituent.

* * * * *